United States Patent [19]

Tecce et al.

[11] Patent Number: 5,130,415
[45] Date of Patent: Jul. 14, 1992

[54] SYNTHETIC PEPTIDE ENDOWED WITH IMMUNOLOGICAL ACTIVITY, CAPABLE OF INDUCING THE PRODUCTION OF ANTIBODIES WITH A HIGH SPECIFICITY TOWARDS ALPHA-FETOPROTEIN, AND THEIR USE IN THE DIAGNOSTIC FIELD

[75] Inventors: Mario F. Tecce, Siena; Marzia M. Giuliani, Colle di Val d'Elsa; Stefano Ricci, Siena; Giulio Ratti, Siena; Benedetto Terrana, Siena, all of Italy

[73] Assignee: Sclavo S.p.A., Siena, Italy

[21] Appl. No.: 384,411

[22] Filed: Jul. 24, 1989

[30] Foreign Application Priority Data

Jul. 29, 1988 [IT] Italy ............... 21553 A/88

[51] Int. Cl.$^5$ .................. C07K 13/00; A61K 37/00
[52] U.S. Cl. .................... 530/324; 530/350; 530/363; 530/380; 424/88; 435/69.7
[58] Field of Search ............ 530/324, 350, 380, 363; 435/69.7; 424/88

[56] References Cited

U.S. PATENT DOCUMENTS 4,223,002 9/1980 Newman ............... 424/101

OTHER PUBLICATIONS

Morinaga et al. (1983) Proc. Natl. Acad. Sci. 80, 4604-4608.
Nicosia et al. (1987) Infect. and Immun. 55, 963-967.
Maniatis et al. (1982) "Molecular Cloning; A Laboratory Manual", CSH, New York, pp. 403-433.

*Primary Examiner*—Robert A. Wax
*Assistant Examiner*—R. Keith Baker
*Attorney, Agent, or Firm*—Hedman, Gibson & Costigan

[57] ABSTRACT

A synthetic peptide endowed with immunological activity is disclosed, which is capable of inducing in mammals the formation of anti-peptide antibodies capable of recognizing human alpha-fetoprotein and of reacting with it, and incapable of recognizing albumin or its degradation products, with said peptide being essentially constituted by the aminoacidic sequence of formula (I), corresponding to 38-119 region of human alpha-fetoprotein.

Furthermore, the methods and means for preparing said peptide by means of the recombinant DNA techniques are reported.

The synthetic peptide (I), like the polyclonal and monoclonal antipeptide antibodies are particularly suitable for the early diagnosis of hepatocellular carcinoma and of teratocarcinoma.

6 Claims, 4 Drawing Sheets

| | | | |
|---|---|---|---|
| AFP | 1 | TLHRNEYGIASILDSYQCTAEISLADLATIFFAQFVQEATYKEVSKMVKD | 50 |
| ALB | 1 | .....DAHKSEVAHRFKDLGEENFKALVLIAFAQYLQQCPFEDHVKLVNE | 45 |
| AFP | 51 | ALTAIEKPTGDEQSSGCLENQLPAFLEELCHEKEILEKYGHSDCCSQSEE | 100 |
| ALB | 46 | VTEFAKTCVADESAENCDKSLHTLFGDKLCTVATLRETYGEMADCCAKQE | 95 |
| AFP | 101 | GRHNCFLAHKKPTPASIPLFQVPEPVTSCEAYEEDRETFMNKFIYEIARR | 150 |
| ALB | 96 | PGRNECFLQHKDDNPNLPRLVRPEVDVMCTAFHDNEETFLKKYLYEIARR | 145 |
| AFP | 151 | HPFLYAPTILLWAARYDKIIPSCCKAENAVECFQTKAATVTKELRESSLL | 200 |
| ALB | 146 | HPYFYAPELLFFAKRYKAAFTECCQAADKAACLLPKLDELRDEGKASSAK | 195 |
| AFP | 201 | NQHACAVMKNFGTRTFQAITVTKLSQKFTKVNFTEIQKLVLDVAHVHEHC | 250 |
| ALB | 196 | QRLKCASLQKFGERAFKAWAVARLSQRFPKAEFAEVSKLVTDLTKVHTEC | 245 |
| AFP | 251 | CRGDVLDCLQDGEKIMSYICSQQDTLSNKITECCKLTTLERGQCIIHAEN | 300 |
| ALB | 246 | CHGDLLECADDRADLAKYICENQDSISSKLKECCEKPLLEKSHCIAEVEN | 295 |
| AFP | 301 | DEKPEGLSPNLNRFLGDRDFNQFSSGEKNIFLASFVHEYSRRHPQLAVSV | 350 |
| ALB | 296 | DEMPADLPSLAADFVESKDVCKNYAEAKDVFLGMFLYEYARRHPDYSVVL | 345 |
| AFP | 351 | ILRVAKGYQELLEKCFQTENPLECQDKGEEELQKYIQESQALAKRSCGLF | 400 |
| ALB | 346 | LLRLAKTYETTLEKCCAAADPHECYAKVFDEFKPLVEEPQNLIKQNCELF | 395 |
| AFP | 401 | QKLGEYYLQNAFLVAYTKKAPQLTSSELMAITRKMAATAATCCQLSEDKL | 450 |
| ALB | 396 | EQLGEYKFQNALLVRYTKKVPEVSTPTLVEVSRNLGKVGSKCCKHPEAKR | 445 |
| AFP | 451 | LACGEGAADIIIGHLCIRHEMTPVNPGVGQCCTSSYANRRPCFSSLVVDE | 500 |
| ALB | 446 | MPCAEDYLSVVLNQLCVLHEKTPVSDRVTKCCTESLVNRRPCFSALEVDE | 495 |
| AFP | 501 | TYVPPAFSDDKFIFHKDLCQAQGVALQTMKQEFLINLVKQKPQITEEQLE | 550 |
| ALB | 496 | TYVPKEFNAETFTFHADICTLSEKERQIKKQTALVELVKHKPKATKEQLK | 545 |
| AFP | 551 | AVIADFSGLLEKCCQGQEQEVCFAEEGQKLISKTRAALGV | 590 |
| ALB | 546 | AVMDDFAAFVEKCCKADDKETCFAEEGKKLVAASQAALGL | 585 |

FIG.1

|     |                                                        | lungh. |
|-----|--------------------------------------------------------|--------|
|     | 5'————————————————————3'                               |        |
| 1.2 | GATCCGACCCGGAAGCCACTTACAAGGAAGTAAGCAAAATGGTGAAAGATG    | 51     |
| 2   | CATTGACTGCAATTGAGAAACCCACTGGAGATGAACAGTC               | 40     |
| 3   | TTCAGGGTGTTTAGAAAACCAGCTACCTGCCTTTCTGGAA               | 40     |
| 4   | GAACTTTGCCATGAGAAAGAAATTTTGGAGAAGTACGGAC               | 40     |
| 5   | ATTCAGACTGCTGCAGCCAAAGTGAAGAGGGAAGACATAACT             | 42     |
| 6.2 | GTTTTCTTGCACACAAAAAGCCCACTCCAGCATCGATCCCACTTTGATA      | 50     |

|      |                                                        |    |
|------|--------------------------------------------------------|----|
|      | 3'————————————————————5'                               |    |
| 7.2  | GCTGGGCCTTCGGTGAATGTTCCTTCA                            | 27 |
| 8    | TTCGTTTTACCACTTTCTACGTAACTGACGTTAACTCTTT               | 40 |
| 9    | GGGTGACCTCTACTTGTCAGAAGTCCCACAAATCTTTTGG               | 40 |
| 10   | TCGATGGACGGAAAGACCTTCTTGAAACGGTACTCTTTCT               | 40 |
| 11   | TTAAAACCTCTTCATGCCTGTAAGTCTGACGACGTCGGTT               | 40 |
| 12   | TCACTTCTCCCTTCTGTATTGACAAAAGAACGTGTGTTTTTCGGG          | 45 |
| 13.2 | TGAGGTCGTAGCTAGGGTGAAACTATTCGA                         | 30 |

FIG.2

```
1.2  GATCCGACCCGGAAGCCACTTACAAGGAAGTAAGCAAAATGGTGAAAGATG
7.2            GCTGGGCCTTCGGTGAATGTTCCTTCA 1.2  GATCCGACCCGGAAGCCACTTACAAGGAAGTAAGCAAAATGGTGAAAGATG
8                                TTCGTTTTACCACTTTCTACGTAACTGACGTTAACTCTTT

2             CATTGACTGCAATTGAGAAACCCACTGGAGATGAACAGTC
8    TTCGTTTTACCACTTTCTACGTAACTGACGTTAACTCTTT  B

2    CATTGACTGCAATTGAGAAACCCACTGGAGATGAACAGTC
9                      GGGTGACCTCTACTTGTCAGAAGTCCCACAAATCTTTTGG

3                      TTCAGGGTGTTTAGAAAACCAGCTACCTGCCTTTCTGGAA
9    GGGTGACCTCTACTTGTCAGAAGTCCCACAAATCTTTTGG

3    TTCAGGGTGTTTAGAAAACCAGCTACCTGCCTTTCTGGAA
10                     TCGATGGACGGAAAGACCTTCTTGAAACGGTACTCTTTCT

4                      GAACTTTGCCATGAGAAAGAAATTTTGGAGAAGTACGGA
10   TCGATGGACGGAAAGACCTTCTTGAAACGGTACTCTTTCT

4    GAACTTTGCCATGAGAAAGAAATTTTGGAGAAGTACGGA
11                     TTAAAACCTCTTCATGCCTGTAAGTCTGACGACGTCGGTT

5                      ATTCAGACTGCTGCAGCCAAAGTGAAGAGGGAAGACATAACT
11   TTAAAACCTCTTCATGCCTGTAAGTCTGACGACGTCGGTT

5    ATTCAGACTGCTGCAGCCAAAGTGAAGAGGGAAGACATAACT
12                     TCACTTCTCCCTTCTGTATTGACAAAAGAACGTGTGTTTTTCGGG 6.2                    GTTTTCTTGCACACAAAAAGCCCACTCCAGCATCGATCCCACTTTGATA
12   TCACTTCTCCCTTCTGTATTGACAAAAGAACGTGTGTTTTTCGGG 6.2  GTTTTCTTGCACACAAAAAGCCCACTCCAGCATCGATCCCACTTTGATA
13.2                  TGAGGTCGTAGCTAGGGTGAAACTATTCGA
```

FIG.3

5' GATCCGACCCGGAAGCCACTTACAAGGAAGTAAGCAAAATGGTGAAAGATGCATTGACTG
GCTGGGCCTTCGGTGAATGTTCCTTCATTCGTTTTACCACTTTCTACGTAACTGAC

CAATTGAGAAACCCACTGGAGATGAACAGTCTTCAGGGTGTTTAGAAAACCAGCTACCTG
GTTAACTCTTTGGGTGACCTCTACTTGTCAGAAGTCCCACAAATCTTTTGGTCGATGGAC

CCTTTCTGGAAGAACTTTGCCATGAGAAAGAAATTTTGGAGAAGTACGGACATTCAGACT
GGAAAGACCTTCTTGAAACGGTACTCTTTCTTTAAAACCTCTTCATGCCTGTAAGTCTGA

GCTGCAGCCAAAGTGAAGAGGGAAGACATAACTGTTTTCTTGCACACAAAAAGCCCACTC
CGACGTCGGTTTCACTTCTCCCTTCTGTATTGACAAAAGAACGTGTGTTTTTCGGGTGAG

CAGCATCGATCCCACTTTGATA         3'
GTCGTAGCTAGGGTGAAACTATTCGA

FIG.4

1    MSKTTKKFNSLCIDLTRDLSLEIYQSIASVATGSGDPHSDDFTAIAYLRD
     +---------++---+

51   ELLTKHPTLGSGNMEATRRTLAIAKLLSWGIRATGSDPEATYKEVSKMVK
     +--+         +-----++------+              +-+

101  DALTAIEKPTGDEQSSGCLENQLPAFLEELCHEKEILEKYGHSDCCSQSE
     +------------------++-------+   +-----+

151  EGRHNCFLAHKKPTPASIPL
     +------++-------+

FIG.7

SYNTHETIC PEPTIDE ENDOWED WITH IMMUNOLOGICAL ACTIVITY, CAPABLE OF INDUCING THE PRODUCTION OF ANTIBODIES WITH A HIGH SPECIFICITY TOWARDS ALPHA-FETOPROTEIN, AND THEIR USE IN THE DIAGNOSTIC FIELD

The present invention relates, in general, to means and to methods which use said means for the determination and the measurement of low seral levels of alpha-fetoprotein in a sample of human blood.

In particular, the present invention relates to a synthetic peptide endowed with immunological activity, which is capable of inducing the formation of anti-peptide antibodies capable of recognizing human alpha-fetoprotein and of reacting with it, and incapable of recognizing albumin or its degradation products.

The present invention relates furthermore to means and methods for the production of such a peptide, and to the use of said synthetic peptide and of the polyclonal and monoclonal anti-peptide antibodies in the diagnostic field for the determination of and the measurement of low serumal levels of human alpha-fetoprotein.

Alpha-fetoprotein (AFP) represents, together with albumin, one of the major serumal proteins normally synthesized during the embryonal and phoetal life of the hepatic cells, by the cells of the vitellicle, and, in smaller amounts, by the cells of the intestinal tract.

Said protein, differently from albumin, disappears after the birth and appears again in the serum of an adult during pregnancy, owing to the presence of the phoetus, and also under pathologic conditions, in particular in the presence of primary malignant of liver neoplasiae and of teratocarinoma.

The determination and the measurement of concentration of AFP in the serum of an adult person could therefore represent a means of considerable clinic usefulness in the early diagnosis of carcinoma.

However, the fact that alpha-fetoprotein was found in the serum of persons affected by inflammatory diseases (acute or chronic hepatitis and cirrhosis) and in the regenerative layers of liver, even if at concentrations lower than as found in cases of carcinoma, considerably limited the use of the test of measurement of the serumal levels of AFP as specific and independent tests for the diagnosis of hepatic neoplasiae in particularly early stages.

In fact, in said stages it is difficult to discriminate between increases in AFP levels due to carcinoma, and those caused by non-neoplastic diseases.

At present, the use of AFP as a tumor marker, wherein by this term a substace is meant, the presence of which in a human biologic sample indicates the presence of a neplasia, relates, above all, to the formulation of the prognosis, in that the plasmatic level of AFP is rather well proportional to the existing neoplastic tissue.

Therefore, a measurement of its concentration iis useful above all in order to monitor the efficacy of a chemotherapeutic or surgical treatment.

Generally, a hepatocellular carcinoma is diagnosed with reliability when in human serum levels of AFP are found, which are of round 300-500 ng/ml, i.e., when the tumor is by now in an advanced stage and a surgical treatment thereof is no longer possible.

Therefore, an important result in this particular sector of the art would consist in the development of a means and of a method for the high-specificity diagnosis of cancer, and this in view, in particular, of the need of an early diagnosis of the hepatic tumor in particular in high-risk populations.

In the art many methods for the determination of AFP in human blood are known, which are essentially based on the use of anti-AFP polyclonal antibodies.

Said methods suffer however from drawbacks deriving both from the heterogeneity of the polyclonal antibodies, and from the difficulty of extracting and purifying them.

It derives therefrom that such methods are not very sensitive, not specific and not feasible from an economic point of view.

Therefore, in the art other methods were proposed for determining AFP in human blood, which are essentially based on the use of monoclonal anti-alpha-fetoprotein antibodies (MAb).

On this subject a large number of literature references, in particular patent literature references, exist, in which immunologic methods for the determination of AFP are described, which use two or more monoclonal anti-AFP antibodies or particular reactants, or particular operating conditions.

In this regard, the following works and patents are cited: Portsman, T. et al. [Clin. Chim. Acta 135:13–22 (1983)]; Brock, D. J. et al. [(Clin. Chim. Acta 122:353–358 (1982)]; Uotila, M. et al. [J. Immun. Methods, 42:11–15 (1981)]; EP 158973.

Unfortunately, such methods are not completely satisfactory, in particular if one considers that the monoclonal antibodies used can show cross-reactions with proteins different from AFP.

In fact, by operating according to the processes known from the prior art, the monocloned anti-AFP antibodies are prepared by means of conventional methods, by using the whole molecule of alpha-fetoprotein as the antigen.

As a consequence, the so obtained MAb's can result specific towards epitopes of AFP which show a high homology with those of albumin.

In fact, the possibility of an immunologic cross-reaction between AFP and albumin has been known for long time [Ruoslhati et al. (1976) P.N.A.S., 73, 4641] and recently the reason for it was identified in the high homology of the aminoacidic sequences in said two proteins [Law et al. (1981), Nature, 291, 201; Marinaga et al. (1983) P.N.A.S., 79, 71].

Therefore, although in the preparation of monoclonal antibodies against alpha-fetoprotein due allowance for such a matter of fact is made by means of suitable controls which secure the specificity of said antibodies, the possibility remains always that a very minor cross-reaction may take place between said two proteins.

Due to the enormously high serumal concentration of albumin, about 50 mg/ml, as compared to the concentration measured when AFP is titrated (up to 20–40 mg/ml), it derives that also this very low cross-reactivity may become significant, thus originating wrong results. In particular, the highest cross-reactivity between said two proteins is observed when albumin is denatured or degraded, probably owing to the exposure of further antigenic determinants, or epitopes, which are recognized by anti-AFP antibodies [Ruoslhati et al. (1976) P.N.A.S., 73, 4641].

Furthermore, the hypothesis was raised that in inflammatory hepatic diseases a general activation may take place of the proteolytic processes capable of increasing the amount of circulation degraded albumin, which might interfere with the titration of alpha-fetoprotein, increasing the found value of is concentration.

Therefore, the need is particularly felt in the art, of having available anti-AFP antibodies, which are incapable of recognizing albumin or its degradation products. This would make it possible such an interference to be substracted in a diagnostic test, thus the sensitivity of such test for neoplastic statuses being increased.

As a consequence, the object of the present invention if of developing sensitive means endowed with high antigenic specificity, as well as methods using such means in order to determine and measure the concentration of alpha-fetoprotein in a sample of human blood.

This object is achieved according to the present invention by providing a synthetic antigen unknown up to now, which makes it possible the problems affecting the prior art to be overcome.

Therefore, a purpose of the present invention is a synthetiic peptide endowed with immunological activity, which is capable of inducing in mammals the formation of anti-peptiide antibodies capable of recognizing human alpha-fetoprotein and of reacting with it, and incapable of recognizing albumin or its degradation products, with said peptide being essentially constituted by the aminoacidic sequence corresponding to 38-119 region of human alpha-fetoprotein.

A further purpose of the present invention are means and methods for preparing said peptide by means of the recombinant DNA techniques.

Another purpose of the present invention is the use of said synthetic peptide for the preparation of polyclonal and monoclonal anti-peptide antibodies capable of recognizing alpha-fetoprotein and of reacting with it, and incapable of recognizing albumin or its degradation products.

Still a further purpose of the present invention are polyclonal and monoclonal anti-peptide antibodies capable of recognizing alpha-fetoprotein and of reacting with it, and incapable of recognizing albumin or its degradation products.

Still another purpose of the present invention are hybridomas capable of producing monoclonal anti-peptide antibodies capable of recognizing alpha-fetoprotein and of reacting with it, and incapable of recognizing albumin or its degradation products.

Still another purpose of the present invention is an immunologic method for the determination and the titration of low seral levels of alpha-fetoprotein in a sample of human blood, which uses said synthetic peptide and/or monoclonal and polyclonal anti-peptide antibodies..

Still another purpose of the present invention is a diagnostic kit for the measurement of the concentration of alpha-fetoprotein in a sample of human blood containing the synthetic peptide and/or polyclonal and monoclonal anti-peptide antibodies capable of recognizing alpha-fetoprotein and of reacting with it, but incapable of recognizing albumin or its degradation products.

Further purposes of the present invention will be evident from the reading of the text and from the following Examples.

The present invention is essentially based on the identification of a region of the aminoacidic sequence of AFP which is immunologically active and sufficiently free from meaningful homologies with albumin.

In particular, said region corresponds to the sequence of AFP which is comprised between the aminoacids from 38 to 119, and is characterized by the aminoacidic sequence (I):

GluAlaThrTyrLysGlyValSerLysMetValLysAsp
AlaLeuThrAlaIleGluLysProThrGlyAspGluGln
SerSerGlyCysLeuGluAsnGlnLeuProAlaPheLeu
GluGluLeuCysHisGluLysGluIleLeuGluLysTyr
GlyHisSerAspCysCysSerGlnSerGluGluGlyArg
HisAsnCysPheLeuAlaHisLysLysProThrProAla
SerIleProLeu.

According to the present invention, a peptide having the above reported sequence can be prepared by means of a chemical synthesis, or by means of biological methods (recombinant DNA).

Said peptide, when is obtained by the recombinant-DNA route, can contain a methionine moiety or a fusion peptide at its aminic chain end.

According to the present invention, the lower homology with albumin is in fact such as to secure the greatest specificity of this peptide which can be used as a substitutive antigenic protein.

The nucleotidic sequences of the genes coding for AFP and albumin, as well as their aminoacidic sequences have been respectively published by Marinaga et al. [(1983), M.N.A.S. 80, 4604] and Dugaiezyk et al. [(1982), P.N.A.S. 79, 71].

A comparison between said two proteins evidenced the presence, along both aminoacidic sequences, of a high homology, which is maximum in domains 2 and 3.

In accordance with the present invention, for the purpose of identifying in the aminoacidic sequence of AFP a region free from corresponding similar groups in albumin, the sequences of both proteins were aligned by using programs for the analysis of different aminoacidic and nucleotidic sequences, for example the program (GAP) published by Devereux, S. et al. [Nucl. Acid Res. 12: 387-395 (1984)].

From among the different alignments so obtained, one was be found (FIG. 1), which made it possible the region of AFP comprised between aminoacids 38 and 119 to be identified as the lowest-homology region with a albumin, and therefore as the region with the highest antigenic specificity.

Furthermore, the analysis of the characterstics of hydrophilicity of the above said region were such, as to make this sequence to be regarded as endowed with good characteristics of immunogenicity.

On the basis of these results, and according to the present invention, useful peptides for the production of antibodies with a high specificity for AFP can be synthetized.

Several methods are available for synthetizing a peptide having these characteristics.

First of all, a peptide can be synthetized by a chemical or a biochemical way, which essentially consists of the sequence of formula (I).

Those peptides which are totally constituted by the (I) sequence are preferred.

According to a form of practical embodiment of the present invention, a peptide of formula (I) can be synthetized by means of a chemical route, according to one of the general techniques known in the art, such as, e.g., the synthesis on solid phase described by Merrifield, R. B. and Marglin, A. [(1970) Annu. Rev. Biochem. 39 841-866].

Of course, with the development of modern synthetizers, many of which are available from the market, synthetizing long peptidic molecules or long peptidic fragments became possible, which are subsequently bonded to each other so as to obtain the peptide containing the desired sequence.

According to another form of practical embodiment of the present invention, a peptide of formula (I) can be obtained by means of recombinant-DNA techniques.

The development of molecular genetics made in fact possible, the union of portions of genetic material from different organisms to be carried out in vitro, thus making it possible new combinations of genes to be formed, and therefore of new hereditary characteristics to be obtained in determined organisms. In general, the techniques of recombinant DNA comprises:

isolating a fragement of DNA which codes for a determined polypeptide;

inserting said fragment in a cloning vector, placing it under the control of regulating sequences [promoter, site of transcription beginning and site of ribosomal recognition (RBS)] and/or of secretion sequences, and isolating the so obtained hybrid vector or molecule of recombinant DNA;

introducing said molecule into a host organism by means of the transformation technique;

cultivating said transformed host organism, so as to obtain the expression of the DNA fragment consisting in the production of the desired polypeptide, and, finally, isolating and purifying from the culture medium or from the host organism the so expressed product.

According to the present invention, the DNA fragment which codes for the 37-119 region of human alphafetoprotein can be obtained from the gene coding for AFP by means of the digestion with suitable restriction enzymes, or by means of the preparation of synthetic oligonucleotides.

According to a form of practical embodiment of the present invention, the filaments of the DNA region which codes for the 38-119 peptide were split up into portions, and synthetic oligonucleotides having a sequence identical to each of said portions were synthetized by means of an automatic synthetizer.

The splitting up of the the nucleotide sequence was carried out in such a way that the complementary portions between the components of both filaments were so staggered, that each oligonucleotide could hibridize simultaneously with other two oligonucleotides.

Figure 4:
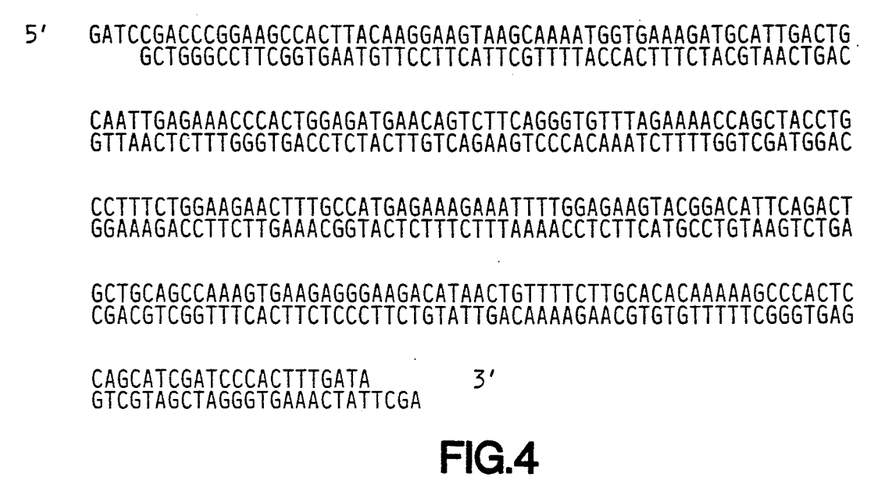
FIG. 4: shows the nucleotidic sequence of the synthetic gene which codes for 38-119 polypeptide obtained by the self-assembly of the oligonucleotides reported in FIG. 2.

As a consequence, by combining the so synthetized oligonucleotides a self-assembly product can be obtained, on the basis of the hybration correspondences, of the same type as shown in FIG. 4.

In practice, the synthetic oligonucleotides can be mixed together with the DNA of a cloning vector previously digested with suitable restriction enzymes, in ligase buffer, in the presence of the T4 DNA-ligase enzyme, so as to obtain, at the end of the reaction, the formation of the self-assembly product, and, simultaneously, its insertion into the cloning vector.

Examples of suitable vectors for the intended purpose can be selected from among plasmids and bacteriophages generally used in the technique of recombinant DNA and available to public.

On accordance with the present invention, the plasmid of *E. coli* pEX34A was used, which contains the gene which codes for resistance to ampicillin and the gene which codes for the DNA polymerase of MS2 phage.

Said plasmid was digested with the restriction enzymes BamHI and EcoRI, which generate single-filament end groups cohesive with those of the product from the self-assembly and was then mixed with the synthetic oligonucleotides in the presence of T4 DNA-ligase enzyme.

The reaction was carried out overnight in buffer solution, at a temperature of, or approximately of, 14° C.

At the end of said reaction times, aliquots of the mixture of ligase were used in order to transform cells of *E. coli* rendered competent by means of the method described by Mandel, M. and Higa [(1970) J. Mol. Biol. 53, 154].

The transformants were subsequently cultivated on a suitable medium such as, e.g., LB, rendered selective by means of the addition of ampicillin. From one of the so obtained positive clones, the recombinant plasmid was then isolated, which contained the fragment of synthetic DNA coding for the 38-119 peptide in exact reading phase with DNA polymerase.

Said plasmid, denominated A1/GTA was deposited as *Escherichia coli* (A1/GTA) with the American Type Culture Collection, and it was given the reference code ATCC 67742).

According to the present invention, the plasmid was used in order to transform cells of *E. coli* K12, ΔH1, Δtrp and the so obtained transformants were used for preparing the desired peptide by operating according to such procedures as described by Nicosia et al. [(1987) Inf. and Immun. 55, 963].

The present invention anyway comprises the use of different strains of *E. coli* such as, e.g., *E. coli* JM 101, *E. coli* 71/18, *E. coli* JM 108 or of other microorganisms, many of which are available for public, or are deposited and are therefore available from recognized Institutes such as, e.g., the American Type Culture Collection.

According to the instant invention, 38-119 peptide was obtained from the bacterial extract as a fused protein, i.e., constituted by a portion of DNA-polymerase and by the 38-119 aminoacidic sequence, in which the portion of DNA-polymerase has the following aminoacidic sequence:

MetSerLysThrThrLysLysPheAsnSerLeyCys
IleAspLeuThrArgAspLeuSerLeuGluIleTyr
GlnSerIleAlaSerValAlaThrGlySerGlyAsp
ProHisSerAspAspPheThrAlaIleAlaTyrLeu
ArgAspGluLeuLeuThrLysHisProThrLeu
GlySerGlyAsnAspGluAlaThrArgArgThr
LeuAlaIleAlaLysLeuLeuSerTrpGlyIle
ArgAlaThrGlySerAspPro.

Said protein was dialysed against 50 nM buffer and was then identified by Western blot with anti-MS2-DNA-polymerase antibodies and anti-human-AFP antibodies.

Figure 6A:
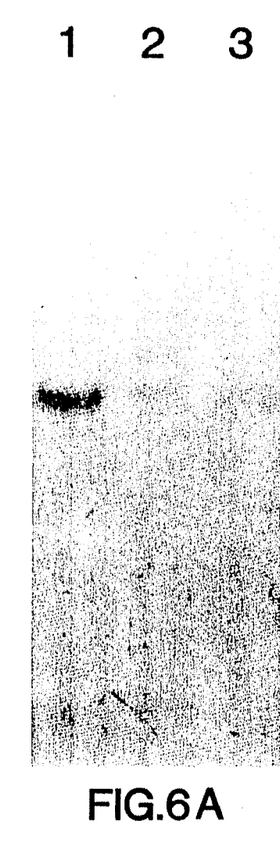
FIGS. 6A and 6B: Western blot of the samples reported in FIG. 5 with specific anti-MS2-DNA-polymerase antibodies (1, 2 and 3 in the first blot) and with specific anti-human-alpha fetoprotein antibodies (4, 5 and 6 in the second blot).
Figure 6B:
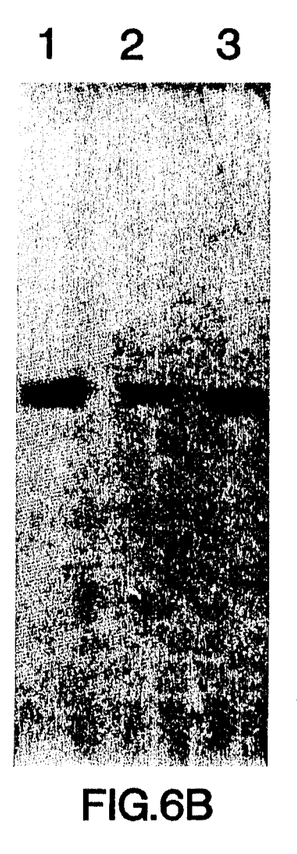

The results reported in FIG. 6 showed, as expected, that the protein in question was recognized by the antibodies directed against both of said proteins, of which it contains portions of sequence.

Figure 5:
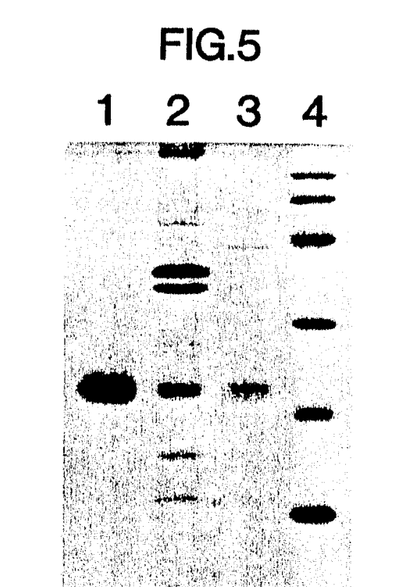

Furthermore, its molecular weight corresponded to about 20 kilodaltons (KD), i.e., to a similar value to as expected on the basis of the nucleotidic sequence (FIG. 5).

In order to confirm the sequence of the so obtained peptide on the basis of direct data, and not only on the basis of a recognition by an antibody, it was submitted to analysis by fast atom bombardment mass-spectrometry after digestion with tripsin.

This technique makes it possible the sequence of the aminoacids to be confirmed on the basis of mass data.

Figure 7:
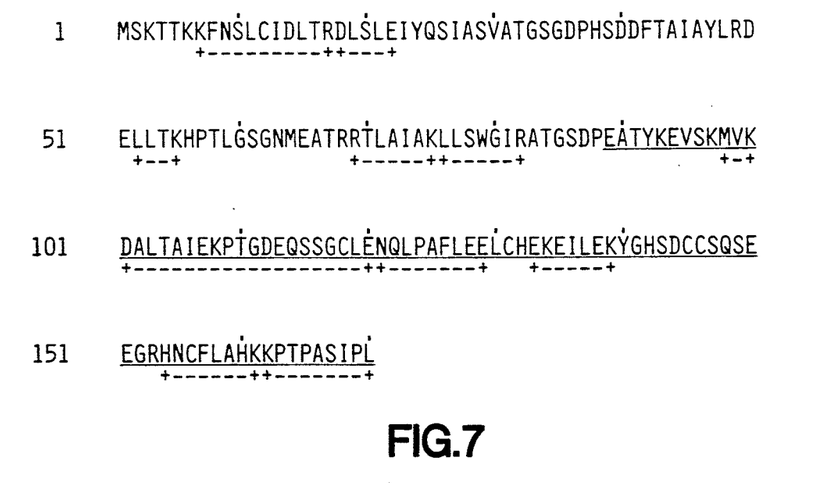
FIG. 7: shows the sequence of the fusion protein as determined by means of mass-spectrometry. The peptides identified by means of said method are underlined (+----+).

FIG. 7 shows the sequence of the fusion protein on the basis of the building of the synthetic gene.

The aminoacidic regions identified by means of mass spectrometry are underlined.

It is evident that, above all as regards the AFP portion, the confirmed regions constitute a very major fraction, also on considering that by means of this methods, seldom more than 60% of the peptidic sequences can be read.

According to the present invention, said fused protein, like the peptides only constituted by the sequence of formula (I) can be used as alpha-fetoprotein-substituting antigens for the production of polyclonal and monoclonal antibodies which do not originate phenomena of cross-reaction with albumin.

In general, the preparation of polyclonal antibodies can be carried out by means of the immunization of such animals as various genera of monkey, horse, ox and animals of the type of ox, sheep, pig, rabbit, winged creatures such as hen, turkey, goose and duck, as well as rat, mice e Guinea pig.

Goat is taken into a particular consideration in order to originate those antibodies which in the presence of AFP and of albumin, or of its degradation products, do not originate phenomena of immunologic cross-reaction.

The immunization of the animals is carried out according to the present invention with the synthetic peptide in its pristine state, or activated, according to well-known general techniques.

The further execution of the immunization and the processing in order to respectively obtain the antisera or the antibodies is carried out by operating according to known techniques.

Also the processing and the preservation of the antisera or of the antibodies take place according to known methods in immunology.

In order to verify the immunogenic properties thereof, the fusion protein was injected into Balb/c mice, as such, or conjugated with hemocyanin, which increases its antigenic power.

The sera drawn from immunized mice were subsequently analysed by means of a radioimmunologic assay in order to verify the production of anti-alpha-fetoprotein antibodies.

The results obtained by using different dilutions of the sera, showed that all of the mice responded positively to the treatment, yielding similar values to those obtained with sera of rabbits immunized with whole AFP molecule. The highest antibody titre was found in case of animals treated with 10 micrograms of conjugated fused protein.

The so obtained data confirms the ability of the peptide according to the present invention to induce the formation of antibodies capable of recognizing and reacting with human alpha-fetoprotein.

According to the present invention, the synthetic peptide (I) can be used for the preparation of monoclonal antibodies endowed with a high specificity for AFP.

For that purposes, any of the techniques can be used, which are generally used in this particular sector, such as, e.g., the technique as described in "Basic Methods in Molecular Biology" by Davis L. G. et al., Elsevier, New York, 1986.

In practice, the peptide obtained as a fused protein was used in order to immunize Balb/c mice and prepare the hybridomas.

From among the different cellular lines (hybridomas) obtained, three—denominated as MG 15, MG 24 and MG 31 —were isolated, which are capable of producing monoclonal antibodies which recognize both the alpha-fetoprotein in its pristine state and fused recombinant fetoprotein, and do not recognize albumin.

Polyclonal and monoclonal antibodies according to the present invention are particularly useful for the development of an immunologic method for the determination of low levels of AFP in human blood.

In particular, suitably radiolabeled antibodies can be used in a radioimmunologic assay (RIA), in an immunofluorimetric assay (IFA) or in an immunoenzymatic assay (ELISA).

Once that the synthetic antigen is available, anyone skilled in the art will be capable of producing the specific antibodies, and of developing assays which use said specific antibodies, in order to titrate low AFP levels.

Within the purposes of the present invention also a diagnostic kit falls, which is designed for the determination of AFP in a human blood sample by means of an immunologic assay, with said kit being characterized in that it contains a synthetic peptide of formula (I) and/or polyclonal or monoclonal anti-peptide antibodies.

Furthermore, a diagnostic kit as hereinabove defined can possibly contains a support and the necessary reactants for the development and the visualization of the reaction product.

In any case, those skilled in the art can easily find, on the basis of the specification of the present invention, the necessary conditions and reactants in order to develop a diagnostic kit for the determination and the titration of AFP.

SHORT DESCRIPTION OF THE FIGURES

FIG. 1: shows an alignment of the sequences of aminoacids of human alpha-fetoprotein (HFP) and of human albumin (ALB). The aminoacids are indicated by means of the single-letter code, in which:

| asp | D | thr | T | glu | E | gly | G |
|-----|---|-----|---|-----|---|-----|---|
| lys | K | ala | A | arg | R | val | V |
| his | H | leu | L | tyr | Y | ileu | I |
| cys | C | met | M | asn | N | pro | P |
| gln | Q | phe | F | ser | S | trp | W |

The vertical line (1) denotes sites with identical aminoacids.

FIG. 2: the nucleotidic sequences is reported, written in 5'-3' direction for one filament, and in 3'-5' direction for the antiparallel filament, of the 13 oligonucleotides synthetized in order to build the synthetic gene which codes for the 38-119 aminoacidic sequence.

FIG. 3: shows the various possible alignments between the synthetic oligopeptides.

FIG. 5: shows a polyacrylamide gel in which:
2 and 3=bacterial extract before and after the dialysis;

4 = molecular weights standard (from up downwards: 94.0 KDa, 67.0 KDa, 43.0 KDa, 20.1 KDa, and 14.4 KDa;

1 = recombinant fusion peptide purified by means of semi-preparative electrophoresis.

By means of the line (———), the sequence of 38-119 peptide is indicated.

The following experimental examples are illustrative and non-limitative of the invention.

EXAMPLE 1

Building the Recombinant Plasmid A1/GTA (A) Identification of 38-119 sequence of alpha-fetoprotein The aminoacidic sequences of alpha-fetoprotein and of albumin were aligned by using the GAP program contained in the software package by the Group of Genetics of University of Wisconsin.

This package consist of a set of programs of analysis of aminoacidic and nucleotidic sequences published by Devereux S. et al. [Nucl. Acid. Res. 12, 387-395 (1984)].

Figure 1:
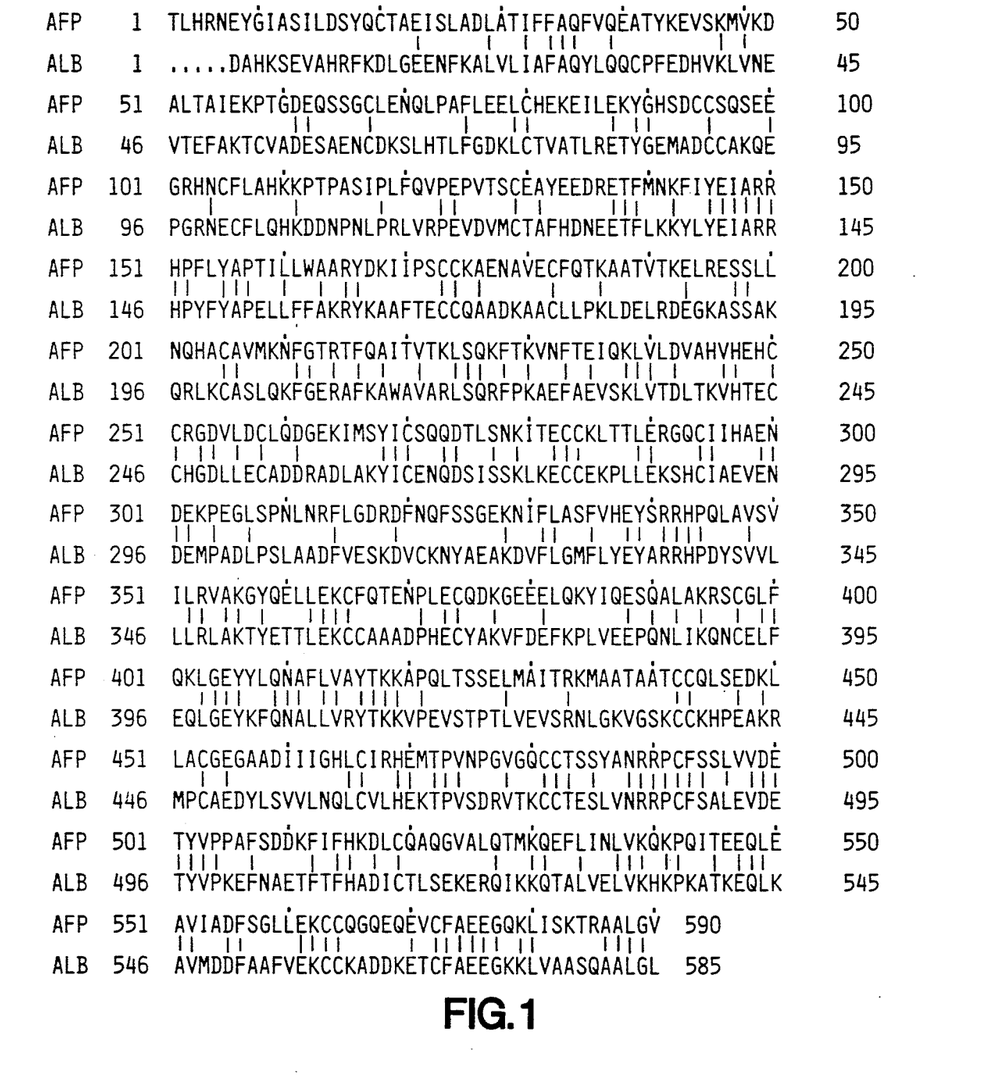

The alignment shown in FIG. 1 represents the best one among all possible alignments between the two proteins, also when only portions of them are taken into consideration, or when the formation of breakages is allowed in each sequence. Using both the GAP program and the Bestfit program, which operates on the basis of a different logics of alignment, no further significant alignments were found between 38-119 sequence of AFP and albumin, as well as the other proteinic sequences described inthe relevant literature.

We can hence conclude that 38-119 sequence does not have a meangingful homology with the above said protiens.

In order to build againt he double-spiral DNA fragment coding for 38-119 peptide, 13 oligonucleotides were synthetized by meahns of the automatic synthetizer System Plus (Beckman). The sequence of said 13 oligonucleotides is shown in FIG. 2, written in 5'-3'direction in case of the one filament, and in 3'-5'direction in case of the antiparallel filament. In FIG. 3 the possible alignments between the above said oligonucleotides are reported. As a consequence, combining all of the oligonucleotides, a product of self-assembly, i.e., a synthetic gene can be obtained on the basis of the correspondences of hybridization, which codes for 38-119 peptide (FIG. 4).

B) Building A1/GTA plasmid, containing the synthetic gene coding for 38-119 peptide 10 micorgrams of pEX34A plasmid was digested for 2 hours in 100 microliters of buffer solution (50 mM Tris-HCL, pH 7.4, 10 mM $MgCl_2$, 50 mM NaCl) at 37° C. in the presence of 30 U (units) of the restriction enzyme BamHI (Boehringer/Mannheim).

The resulting mixture was kept standing at room temperature (20°-25° C.) for 15 minuts, and was then digested with 30 U of restriction enzyme HindIII at 37° C. for two hours.

The enzymatic reaction was then deactivated by keeping the reaction mixture heated at 65° C. for 15 minutes.

The digestion mixture was then charged to a 1.5% agarose gel and was then run for 3.5 hours at 70 Volts.

The BamHI-HindIII fragment, of approximately 6000 base-pairs nbp) ws then electroeluted by operating according to the method by Maniatis (Molecular Cloning: A Laboratory Manual, Cold Spring Harbor, 1982).

250 ng of said fragment was mixed with 5000 ng of each synthetic oligonu cleotide in 30 microliters of ligase mixture in the presence of 1 U of T4 DNA-ligase at 14° C.; the mixture was left standing overnight. The ligase mixture was then used in order to transform cells of *Escherichia coli* K12, ΔH1, Δtrp, rendered competent with 50 mM $CaCl_2$, as reported by Mandel, M. and Higa [(1970) J. Mol. Biol. 53, 154].

The selection of the transformants was carried out on slabs of LB agar medium [10 g/l Bacto Tryptone (DIFCO), 5 g/l Bacto Yeast Rxtract (DIFCO), 10 g/l NaCl], to which 30 micrograms/ml of ampicillin was added, at 30° C., for 18 hours.

The recombinant plasmids extracted from the so obtained clones were then analysed so as to verify the exact nucleotidic sequence.

The recombinant plasmid A1/GTA was so identified, in which the synthetic gene was inserted in BamHI and HindIII sites in the same pahse of reading of polymerase of MS2 phage.

EXAMPLE 2

Expression of the Synthetic Gene

Cells of *Escherichia coli* transformed with the hybrid plasmid A1/GTA were cultivated in 20 mol of LB (1% bactotryptone, 0.5% bacto-yeast extract, 1% NaCL, pH 7.5), overnight at 30° C.

Subsequently, 10 ml of said culture was diluted to 400 ml with the same LB medium, and was then maintained for 2 hours at 30° C. for 2,5 hours and 30 minutes at 42° C. The culture was then centrifuged at 5,000 rpm for 10 minutes in a Becikman trunk centrifuge and the so separated cells were suspended again in 3 ml of a solution at 25% of saccharose, 10 mM Trsi pH 8, 1 mM EDTA.

To the so obtained mixture, lysozyme (100 microliters of a soluction of 40 mg/ml) and 0.8 ml of 0.5 M EDTA were then added.

After 30 minutes of incubation at 37° C., 8 ml of a lysis buffer (1% Triton X-100, 50 mM Tris pH 6, 63 mM EDTA) was added.

The resulting mixture was maintained for 15 minutes inside an ice bath, and for 30 minutes at 37° C. The cells were then sonicated and centrifuges at 8,000 rpm for 30 minutes.

The pellet was then suspended again in 5 ml of 1M urea, wsa maintained at 37° C. for 30 minutes, was centrifuged as hereinabove reported, and was suspended again in 5 ml of 7M urea.

The proteinic extract was then dialysed against 50 mM Tris buffer poH 7.0.

during the dialysis, a large number of the bacterial proteins precipitate, whilst the fusion protein remains in solution.

The proteinic extract, considerably enriched with the interesting protein, was checked by means of an electrophoretic run on a polyacrylamide gel prepared according to the procedure by Laemmli [(1970) Nature 227, 680].

The gels were run at 30–35 mA/gel for 8 hours in 0.0246M Tris buffer, 0.19M glycine, pH 8.3, 1% sodium dodecylsulfate (SDS).

At the end of the electrophoretic run, the fusion proteins were visualized by staining the gel with Coomassie blue (0.05% Coomassie blue, 52% methanol, 7% acetic acid) and subsequently decolourising with 6.31% methanol, 7% acetic acid (FIG. 5).

The obtained material is sufficiently enriched with fusion peptide, which represent 80–90% of the material visible in the electrophoretic channel.

The peptide was furthermore identified by Western blot with anti-MS2-DNA-polymerase antibodies and with anti-alpha-fetoprotein antibodies (FIG. 6).

The peptide was recognized by antibodies directed against both of the proteins of which it contains sequence portions.

EXAMPLE 3

Preparation of Synthetic Polyclonal-Anti-peptide-Antibodies

8 Balb/c mice of male sex, 2–3 weeks old, were immunized by intraperitoneal way with the fusion peptide obtained as disclosed in Example 3, and with the same peptide conjugated with hemocyanin.

In practice, the conjugation was carried out by mixing same amounts (by weight) of recombinant protein and hemocyanin (Keyhole limpet hemocyanin, Sigma) (KLH) powder in a volume of 1 ml of PBS, in the presence of glutaraldehyde to an end concentration of 0.5%, and incubating the resulting mixture at room temperature (20°–25° C.) for 1 hour.

The conjugation product was subsequently dialysed against 50 mM Tris buffer pH 7.0, 10 micrograms and 40 micrograms of the recombinatn peptide, either conjugated with hemocyanin or not, were diluted in 100 microliters of PBS buffer and the solutions were diluted to 200 microliters with complete Freund's coadjuvant.

The so obtained solutions were then used in order to immunize the mice by introperitoneal way according to the following scheme:

1st Treatment 1. 2 mice with the conjugated peptide (10 micrograms) to which the complete Freund's coadjuvant was added.
2. 2 mice with the conjugated peptide (40 micrograms) to which the complete Freund's coadjuvant was added.
3. 2 mice with the recombinant peptide (10 micrograms) to which the complete Freund's coadjuvant was added.
4. 2 mice with the recombinant peptide (40 micrograms) to which the complete Freund's coadjuvant was added.
5. 2 mice with 200 microliters of PPS buffer (control groupe).

15 days later, the mice were treated as above reporteed, using 100 microliters od incomplete Freund's adjuvant (2nd treatment).

The same treatment was repeated twice more, with an interval of 15 days.

At the end, the sera drawn from the immunised mice were diluted 1:10 in PBS (0.4% KCL, 0.4% $KH_2PO_4$, 16% NaCl, 2.3% $Na_2HPO_4$) containing 0.5% of gelatin, and the various dilutions were tested by means of a radioimmunologic test (RIA) in order to verify the production of anti-alpha-fetoprotein antibodies.

In practice, on polystyrene slabs with 96 flat-bottom wells alpha-fetoprotein was absorbed by applying 100 microliters of a solution containing 20 micrograms of alpha-fetorprotein/ml in PBS, and maintaining them at room temperature for 2 hours.

The slabs were washed 4 times with 200 microliters of PBS and were then saturated with 0.5% of gelatin in the same buffer for 1 hour at 37° C.

After a washing carried out as above reported, to each well 100 microliters of the diluted serum was charged.

After two hours at room temperature, a further wash was carried out and then 100 microliters/well of anti-immunoglobulin antibodies of mouse or of rabbit in PBS radiolabeled with $^{125}I$ was added to each well (80,000 cpm/well).

The slabs were maintained at 37° C. for 2 hours, were washed with PBS and were then examined in order to count the radioactivity per well.

In this titration, the counts per minute (cpm) increase with increasing concentration of anti-alpha-fetoprotein immunoglobulins in the sera.

The results obtained for the various dilutions, compared to those obtained on non-treated mice (preimmune mice) are the following:

| Serum Dilutions | Pre-immune cpm | 10 µg cpm | 10 µg/KLH cpm | 40 µg cpm | 40 µg/KLH cpm |
| --- | --- | --- | --- | --- | --- |
| 1:10 | 1746 | 5390 | 10830 | 10880 | 626 |
| 1:100 | 769 | 2057 | 7652 | 5730 | 4242 |
| 1:1000 | 479 | 711 | 4310 | 2259 | 3226 |

All of mice respond positively to the treatment, yielding values similar to those obtained by analysing sera of rabbits immunised with the whole molecule of alpha-fetoprotein.

In the same type of titration, in fact, a control serum prepared in rabbit by injecting alpha-fetoprotein gave the following results:

| Serum Dilution | Not treated cpm | Control cpm |
| --- | --- | --- |
| 1:250 | >100 | 3644 |
| 1:500 | >100 | 3257 |
| 1:1000 | >100 | 3021 |

The highest antibody titre was observed in the serum of mouse treated with 10 micrograms of conjugated peptide.

This type of antiserum is hence efficacious in recognizing alpha-fetoprotein with the advantage that it was prepared with a molecule fragment free from homologies with albumin.

EXAMPLE 4

Preparation of Monoclonal Anti-alpha-fetoprotein Antibodies

A group of Balb/c mice were immunized with the synthetic fusion peptide, by operating as reported in Example 3.

The spleens of the mice were subsequently drawn and were used in order to prepare hybridomas according to such techniques as described in "Basic Methods in Molecular Biology" by Davis L. G., Dibner M.D. and Battery J. F., Elservier, N.Y., 1986.

The so obtained fusion products were then analysed by means of a radioimmunologic assay, as reported in above Example 3, in order to determine their capability of recognizing the alpha-fetoprotein, the fusion peptide and albumin.

A hybridoma was thus identified (No. 29), which resulted to recognize both alpha-fetoprotein and the fusion peptide, but not albumin.

This hybridoma was then submitted to two successive clonings by dilution.

In Table I, some Examples of hybridomas are reported, which were analysed after the first cloning for their activity against AFP, the recombinant protein and albumin by means of the radioimmunologic assay as disclosed in Example 3.

The reported values are the average values obtained from two results for each untreated myeloma supernatant.

Some of these hybridomas were submitted to a subsequent cloning, which made it possible the cellular lines MG 15, MG 24, deriving from 29.1 and MG 31, deriving from 29.3, to be selected.

These three hybridomas (MG 15, MG 24 and MG 31) represent Examples of surely monoclonal, antibody-secreting cellular lines which display a very good recognizing of alpha-fetoprotein and of the fused recombinant protein, without recognizing albumin or its degradation products. Said cellular lines were used in order to treat Balb/c mice by intraperitoneal way (about 2,000,000 cells per mouse) and from the resulting ascites the antibodies were purified by passage on A-Sepharose proteinic column according to techniques generally used for hybridomas.

The monoclonal antibodies obtained from these three hybridomas belong all to IgG1 subclass, and were characterized for their AFP-binding power and for their affinity constant. In particular, in order to determine the AFP-binding power of these antibodies, lyso-phase columns (SCLAVO) were used, which contained Sepharose-mouse-anti-gamma-globulins, to which 200 microlitres of the antibody to be assayed, at different contentrations in a Tris-HCl buffer, pH 8.6 (100 mM Tris, 20 mM EDTA, 0.5% NMS, 0.1% BSA), 200 microlitres of $^{125}$I-AFP (total cpm=45,000) and 200 microlitres of Tris buffer pH 8.6 were charged.

The columns were then maintained at room temperature (20°-25° C.) for 2 hours and, after allowing the liquid phase to percolate, were washed with 2 ml of the washing solution, and were counted.

The three monoclonal antibodies showed a binding power of 50% at the concentration of 0.1 micrograms/ml.

The affinity constant was determined by using the same columns, to which 200 microlitres of antibody at the concentration at which their binding power was of about 30%, 200 microlitres of AFP diluted in Tris buffer pH 8.6 at increasing concentrations from 1 ng/ml up to 1,000 ng/ml, and 200 microlitres of $^{125}$I-AFP were charged. After two hours at room temperature, the liquid was made percolate and the columns were washed and counted.

The affinity constants were determined by Scatchard analysis (Scatchard G., 1949, Ann. N.Y. Acad. Sci., 51, 660).

All of said three antibodies have an affinity constant comprised within the range of from 4 to $5+10^{-9}$ l/mol, which result to be very good values for anti-AFP-antibodies, as compared to the best antibodies available from the market.

Furthermore, the possibility of attack of these monoclonal antibodies in solid phase was verified by using buffers at pH values comprised within the range of from 4 to 9.

The three so-characterized antibodies represent an example of monoclonal antibodies which are obtained by using the peptide according to the present invention for immunizing mice and then selecting the clones, and which can be used for the development of a kit for the titration of human AFP.

TABLE 1

| Hybridoma | Activity (cpm) | | |
|---|---|---|---|
| No. | AFP | Fusion Protein | Albumin |
| 29.1 | 5.408 | 10.488 | <0 |
| 29.2 | 5.563 | 9.638 | 59 |
| 29.3 | 5.239 | 6.615 | 50 |
| 29.4 | 7.791 | 9.879 | <0 |
| 29.5 | 8.363 | 10.406 | <0 |
| 29.9 | .6.998 | 9.101 | <0 |
| 29.10 | 7.829 | 8.606 | 80 |

We claim:

1. Synthetic immunogenic peptide which induces the formation of antibodies which recognize human alpha-fetoprotein and which do not recognize albumin or its degradation products, said peptide consisting essentially of the amino acid sequence corresponding to region 38-119 of human alpha-fetoprotein, as defined by the sequence:

GluAlaThrTyrLysGluValSerLysMetValLysAsp
AlaLeuThrAlaIleGluLysProThrGlyAspGluGln
SerSerGlyCysLeuGluAsnGlnLeuProAlaPheLeu
GluGluLeuCysHisGluLysGluIleLeuGluLysTyr
GlyHisSerAspCysCysSerGlnSerGluGluGlyArg
HisAsnCysPheLeuAlaHisLysLysProThrProAla
SerIleProLeu.

2. Synthetic peptide according to claim 1, in which the sequence has a methionine moiety at the amino terminus.

3. Synthetic peptide according to claim 1, in which the sequence has a fusion peptide at the amino terminus.

4. Synthetic peptide according to claim 3, wherein the fusion peptide comprises a portion of DNA polymerase of MS2 phage of *Escherichia coli* comprising the sequence:

MetSerLysThrThrLysLysPheAsnSerLeyCys
IleAspLeuThrArgAspLeuSerLeuGluIleTyr
GlnSerIleAlaSerValAlaThrGlySerGlyAsp
ProHisSerAspAspPheThrAlaIleAlaTyrLeu
ArgAspGluLeuLeuThrLysHisProThrLeu
GlySerGlyAsnAspGluAlaThrArgArgThr
LeuAlaIleAlaLysLeuLeuSerTrpGlyIle

-continued
ArgAlaThrGlySerAspPro.

by means of ligating a cloning vector with a DNA fragment comprising the nucleotide sequence

```
5' GATCCGACCCGGAAGCCACTTACAAGGAAGTAAGCAAAATGGTGAAAGATGCATTGACTG
   GCTGGGCCTTCGGTGAATGTTCCTTCATTCGTTTTACCACTTTCTACGTAACTGAC

CAATTGAGAAACCCACTGGAGATGAACAGTCTTCAGGGTGTTTAGAAAACCAGCTACCTG
   GTTAACTCTTTGGGTGACCTCTACTTGTCAGAAGTCCCACAAATCTTTTGGTCGATGGAC

CCTTTCTGGAAGAACTTTGCCATGAGAAAGAAATTTTGGAGAAGTACGGACATTCAGACT
   GGAAAGACCTTCTTGAAACGGTACTCTTTCTTTAAAACCTCTTCATGCCTGTAAGTCTGA

GCTGCAGCCAAAGTGAAGAGGGAAGACATAACTGTTTTCTTGCACACAAAAAGCCCACTC
   CGACGTCGGTTTCACTTCTCCCTTCTGTATTGACAAAAGAACGTGTGTTTTCGGGTGAG

CAGCATCGATCCCACTTTGATA      3'
   GTCGTAGCTAGGGTGAAACTATTCGA ,
```

5. Synthetic peptide according to claim 1, obtained by means of a fermentation process which comprises cultivating on a suitable culture medium containing carbon sources, nitrogen sources and mineral salts, a transformed microorganism selected from the group consisting of *Escherichia coli, Bacillus*, yeasts and mammal cells transformed with a molecule of recombinant DNA, wherein the molecule of recombinant DNA is obtained in which said DNA fragment is positioned under the control of regulation sequences.

6. Synthetic peptide according to claim 4, obtained by means of a fermentation process which comprises cultivating on a suitable culture medium containing carbon sources, nitrogen sources and mineral salts, a transformed microorganism as deposited with American type culture collection as ATCC 67742.

* * * * *